US006468308B1

(12) United States Patent
Kuberasampath et al.

(10) Patent No.: US 6,468,308 B1
(45) Date of Patent: *Oct. 22, 2002

(54) SYNTHETIC BONE MATRIX

(75) Inventors: Thangavel Kuberasampath, Medway; Lawrence Berlowitz Tarrant, Harvard, both of MA (US)

(73) Assignee: Stryker Corporation, Kalamazoo, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/104,865

(22) Filed: Jun. 25, 1998

Related U.S. Application Data

(60) Continuation of application No. 08/443,676, filed on May 18, 1995, now Pat. No. 6,077,988, which is a division of application No. 07/529,852, filed on May 29, 1990, now Pat. No. 5,645,591.

(51) Int. Cl.$^7$ ................................................. A61F 2/28
(52) U.S. Cl. ................................ 623/16.11; 623/11.11; 623/23.72
(58) Field of Search ........................... 623/11, 12, 16, 623/1, 18, 66; 424/423, 424, 425, 426; 530/350; 435/69.1, 283.1, 284.1

(56) References Cited

U.S. PATENT DOCUMENTS

| | | | |
|---|---|---|---|
| 3,551,560 A | 12/1970 | Thiele | 424/95 |
| 3,855,638 A | 12/1974 | Pilliar | 128/92 |
| 4,172,128 A | 10/1979 | Thiele et al. | |
| 4,280,954 A | 7/1981 | Yannas et al. | 260/123 |
| 4,294,753 A | 10/1981 | Urist | 260/112 |
| 4,350,629 A | 9/1982 | Yannas et al. | 260/123 |
| 4,378,224 A | 3/1983 | Nimni et al. | 8/94 |
| 4,394,370 A | 7/1983 | Jeffries | |
| 4,418,691 A | 12/1983 | Yannas et al. | 128/156 |

(List continued on next page.)

FOREIGN PATENT DOCUMENTS

| | | |
|---|---|---|
| EP | 0069260 | 6/1982 |
| EP | 0148155 | 2/1985 |
| EP | 148155 | 7/1985 |
| EP | 0170979 | 7/1985 |
| EP | 0182488 | 8/1985 |
| EP | 0169001 | 1/1986 |
| EP | 0230647 | 12/1986 |
| EP | 0212474 | 4/1987 |
| EP | 0309241 | 3/1989 |
| EP | 309241 | 3/1989 |
| GB | 1515963 | 6/1978 |
| GB | 2178447 | 11/1987 |
| GB | 2215209 | 9/1989 |
| WO | 8600525 | 1/1986 |
| WO | 8800205 | 1/1988 |
| WO | 8909787 | 10/1989 |
| WO | 9000060 | 1/1990 |

OTHER PUBLICATIONS

Glowacki et al. (May 2, 1981) The Lancet, pp. 959–963.
Sampath et al. (1981) Proc. Natl. Acad. Sci., (USA), vol. 78, pp. 7599–7603.
Sampath and Reddi, (1983) Proc. Natl. Acad. Sci., (USA), vol. 80, pp. 6591–6595.
Sampath and Reddi (1985).

(List continued on next page.)

*Primary Examiner*—David J. Isabella
(74) *Attorney, Agent, or Firm*—Testa, Hurwitz & Thibeault, LLP

(57) ABSTRACT

Disclosed is an osteogenic device capable of inducing the formation of endochondral bone in a shape conforming substantially to the shape of the device when implanted in a mammalian host. The device includes an osteogenic protein dispersed within a porous matrix comprising a polymer of collagen and glycosaminoglycan cross-linked to an $M_C$ value of about 800 to about 60,000. Also disclosed are a method of inducing mammalian bone growth, and a method of inducing conductive bone growth from viable mammalian bone.

15 Claims, 1 Drawing Sheet

U.S. PATENT DOCUMENTS

| | | |
|---|---|---|
| 4,448,718 A | 5/1984 | Yannas et al. ............... 260/123 |
| 4,458,678 A | 7/1984 | Yannas et al. ............... 128/155 |
| 4,505,266 A | 3/1985 | Yannas et al. ................. 128/1 |
| 4,544,516 A | 10/1985 | Hughes et al. ............. 264/108 |
| 4,563,350 A | 1/1986 | Nathan et al. ................ 424/95 |
| 4,563,489 A | 1/1986 | Urist |
| 4,614,794 A | 9/1986 | Easton et al. ............... 530/356 |
| 4,627,853 A | 12/1986 | Cambell et al. .............. 623/16 |
| 4,657,548 A | 4/1987 | Nichols |
| 4,661,111 A | 4/1987 | Ruoslanti et al. .............. 623/1 |
| 4,725,671 A | 2/1988 | Chu et al. |
| 4,787,900 A | 11/1988 | Yannas .......................... 623/1 |
| 4,789,663 A | 12/1988 | Wallace et al. ............... 514/21 |
| 4,795,467 A | 1/1989 | Piez et al. .................... 623/16 |
| 4,812,120 A | 3/1989 | Flanagan et al. |
| 4,837,285 A | 6/1989 | Berg et al. .................. 530/356 |
| 4,880,429 A | 11/1989 | Stone .......................... 623/18 |
| 5,007,934 A | 4/1991 | Stone .......................... 623/20 |

OTHER PUBLICATIONS

Deatherage et al. (1987) Collagen Rel. Res., vol. 7, pp. 225–231.

Deatherage et al. (1988) Int. J. Oral Maxillofac. Surg.. vol. 17, pp. 395–399.

Wang et al., (1988) Proc. Natl. Acad. Sci., (USA), vol. 85, pp. 9484–9488.

Reddi, "Cell Biology and Biochemistry of Endochondral Bone", Coll. Res., vol. 1:209–226.

Spector, J. arthroplasty, vol. 2–1987, pp. 163–177, "Historical Review of Porous–coated Implants".

Strand et al., Biotech, Bioeng, Bioeng., vol. 26/1984, pp. 503–507, "A Modified Matrix Perfusion . . . ".

Aspenberq et al., J. Bone Joint Surg., vol. 70/1988, pp. 625–627 Hydroxyapatite–Coated . . . .

Urist et al., Clin. Orthoped. Rel. Res., vol. 187/1984, pp. 277–280, "B–Rricelcium Phosphate Delivery System . . . ".

Cook et al., Clin. Orthoped. Rel. Res. vol. 232/1998 pp. 225–243 "Hydroxyapatite–Coated Titanium. . . ".

SYNTHETIC BONE MATRIX

REFERENCE TO RELATED APPLICATIONS

This application is a rule 1.53(b) continuation of U.S. Ser. No. 08/443,676, filed May 18, 1995, now U.S. Pat. No. 6,077,988, which is a divisional of U.S. Ser. No. 07/529,852, filed May 29, 1990, now U.S. Pat. No. 5,645,591, the disclosures of which are herein incorporated by reference.

BACKGROUND OF THE INVENTION

This invention relates to osteogenic devices, and more specifically to synthetic implants which induce osteogenesis in vivo. More particularly, this invention relates to biocompatible, bioresorbable, synthetic matrices which promote endochondral bone growth in vivo.

The potential utility of an osteogenic device capable of inducing endochondral bone formation in vivo has been recognized widely. It is contemplated that the availability of such a device would revolutionize orthopedic medicine, certain types of plastic surgery, and various periodontal and craniofacial reconstructive procedures.

The developmental cascade of bone differentiation in mammalian bone tissue is well documented in the art (Reddi (1981) Collagen Rel. Res. 1:209–226). Though the precise mechanisms underlying the phenotypic transformations are unclear, it has been shown that the natural endochondral bone differentiation activity of bone matrix can be dissociatively extracted and reconstituted with inactive residual collagenous matrix to restore full bone inducing activity (Sampath et al. (1981), Proc. Natl. Acad. Sci. USA 78:7599–7603).

Mammalian bone tissue is known to contain one or more active factor(s) which are proteinaceous materials capable of inducing the developmental cascade of cellular events resulting in endochondral bone formation. This active factor has variously been referred to in the literature as bone morphogenetic or morphogenic protein, bone inductive protein, osteogenic protein, osteogenin, or osteoinductive protein. Recently, the protein factors referred to as osteogenic protein (OP) responsible for inducing osteogenesis have been purified, expressed in recombinant host cells, and shown to be truly osteoinductive when appropriately sorbed onto a matrix. (U.S. patent application Ser. No. 179,406).

Studies have shown that while osteoinductive proteins are active cross species, the collagenous bone matrix heretofore required for inducing endochondral bone formation is species specific (Sampath and Reddi (1983) Proc. Natl. Acad. Sci. USA 80:6591–6594). Implants of demineralized, extracted xenogenic bone matrix and OP invariably have resulted in a strong inflammatory response that has inhibited osteogenesis, presumably due to immunogenic protein components in the bone matrix. Hence, osteoinduction requiring the use of allogenic bone matrix is a serious limitation with respect to human clinical use, as human bone is neither readily available nor cost effective.

The current state of the art of materials used in surgical procedures requiring conductive bone repair, such as the recontouring or filling in of osseous defects, is disclosed by Deatherage (J. Oral Maxillofac. Surg. (1988) 17:395–359). All of the known implant materials described (hydroxlapatite, freeze-dried bone, or autogenous bone grafts) have little or no osteoinductive properties. Clearly, the ability to induce osteogenesis is preferred over bone conduction for most procedures.

U.S. Pat. No. 4,795,467 discloses a bone repair composition comprising calcium phosphate minerals and a telopeptide, reconstituted, cross-linked fibrillocollagen. U.S. Pat. No. 4,563,350 discloses an osteogenic device comprising a bone-inducing extract and a collagenous matrix composed of approximately 90% trypsinized bovine bone matrix and 10% bovine dermal collagen. U.S. Pat. No. 4,789,663 discloses a method of effecting conductive bone repair comprising exposing the defect to fresh bone, and using xenogenic collagen from bone and/or skin, wherein the collagen is enzymatically treated to remove telopeptides, and is artificially cross-linked. EPO 309,241 discloses a device for inducing endochondral bone formation comprising an osteogenic extract, and a matrix carrier comprising 60–90% mineral component and 2–40% collagen. Deatherage et al., (Collagen Rel. Res. (1987) 7:2225–2231) purports to disclose an apparently xenogenic implantable device comprising a bovine bone matrix extract and Type 1 human skin collagen. Co-pending patent application Ser. No. 422,613, filed Oct. 17, 1989, entitled "Bone Collagen Matrix for Xenogenic Implants," discloses a xenogenic bone implant prepared from demineralized bovine bone and including osteogenic protein.

It is an object of this invention to provide a biocompatible, biodegradable bone matrix, implantable in a mammalian host with no significant inhibitory immunogenic response. Another object is to provide a matrix which is biocompatible, biodegradable, and which is capable of inducing osteogenesis when incorporated with osteogenic protein in mammals, including humans. Still another object is to promote conductive bone growth in mammals, including humans. Yet other objects are to provide a superior material for coating implantable prothetic devices, and to increase the cellular ingrowth into such devices. Yet another object of the invention is to provide a method for the production of such matrix material.

These and other objects and features of the invention will be apparent from the description, drawings, and claims that follow.

SUMMARY OF THE INVENTION

It has been discovered that osteogenic protein dispersed within a porous, bioresorbable matrix including collagen and glycosaminoglycan is capable of inducing osteogenesis in vivo. This knowledge has been exploited to develop novel osteogenic devices disclosed herein which induce the formation of endochondral bone in a mammalian host in a shape conforming substantially to the shape of the device. The devices may also be used as a surface coating for implantable prosthetic devices to promote cellular ingrowth.

The porous matrix of the osteogenic device includes a cross-linked polymer of collagen and glycosaminoglycan. Collagen is a major protein constituent of connective tissue in vertebrates and invertebrates. Type I collagen, Type II collagen, or mixtures thereof are preferable as the matrix material of the osteogenic device. Preferably collagen comprises about 80–95% by weight of the matrix.

Glycosaminoglycans (GAGs) are mucopolysaccharides of animal origin. They are made up of residues of hexosamines glycosidically bound and alternating in a more-or-less regular manner with either hexuronic acid or hexose moietites. GAGs preferably make up at least about 5%, and more preferably, from about 6% to about 15% by weight of the polymer. Useful GAGs include those comprising sulfate groups such as chondroitin 4-sulfate, chondroitin 6-sulfate, hyaluronic acid, dermatan sulfate, keratan sulfate, heparin, heparan sulfate and combinations thereof. Preferably the matrix includes chondroitin 6-sulfate.

The collagen-GAG polymer is cross-linked to control the solubility and mechanical properties of the matrix. It has been determined that cross-linking the matrix to an $M_C$ value (number average molecular weight between cross-links) of about 800 to about 60,000, and preferably to an $M_C$ of between 5,000 and 10,000, is most beneficial for the osteogenic device.

The invention is embodied as a method of growing bone by conduction including contacting a viable mammalian bone with the cross-linked collagen-GAG matrix. Bone conduction is the growth of bone from existing viable bone, and involves the migration of osteoblasts from the bone to an area immediately adjacent the bone. In one aspect of the invention the matrix material is provided as a coating on an implant placed in contact with viable bone. Useful implants are composed of an inert material such as ceramic, metal, or polymer. In another aspect of the invention, conductive bone growth is induced from a viable mammalian bone by contacting the bone with matrix material into which has been dispersed a glue in an amount sufficient to solidify the matrix when implanted in a mammal or when placed at 37° C. A useful glue is methyl cellulose. The matrix solidifies substantially in the shape of the implanted matrix.

In an alternative embodiment, osteogenic protein is dispersed within the porous matrix. Osteogenic protein comprises a pair of subunits constituting a stable dimer under oxidizing conditions. The protein may be produced using recombinant DNA techniques or may be an extract or naturally sourced purified material. In a preferred aspect, one of the subunits of this protein has an amino acid sequence sufficiently duplicative of the amino acid sequence of OP1, disclosed herein, such that the subunit, when in combination with a second suitable subunit under oxidizing conditions, induces endochondral bone in a mammal when disposed within said matrix implanted in the mammal. OP1 is a protein subunit having the amino acid sequence set forth below.

```
     1        10        20        30        40
     STGSKQRSQNRSKTPKNQEALRMANVAENSSSDQRQACKK 50        60        70        80
     HELYVSFRDLGWQDWIIAPEGYARYYCEGECAFPLNSYMN 90       100       110       120
     ATNHAIVQTLVHFINPETVPKPCCAPTQLNAISVLYFDDS

130
     SNVILKKYRNMVVRACGCH
```

When OP1 is dimerized to form a homodimer or a heterodimer with certain other protein sequences, it can induce endochondral bone formation.

Another aspect of this invention involves methods of producing the osteogenic device which contains osteogenic protein. The method includes providing a porous matrix comprising a polymer of collagen and GAG cross-linked to an $M_C$ value of about 800 to about 60,000; and dispersing within the matrix an osteogenic protein in an amount sufficient to induce endochondral bone formation substantially in the shape of the matrix when implanted in a host.

The dispersing step may include dispersing the osteogenic protein in a solvent such as buffered saline or acetonitrile. If insoluble collagen is to be incorporated into the matrix, it, too, may be dispersed in the solvent. In one aspect of the invention, the solvent is an acidified, aqueous solution containing about 30% to about 55% acetonitrile, and preferably about 50% acetonitrile. The dispersion step may be conducted by dehydrating a mixture including the osteogenic protein and particles of the collagen-GAG polymer. Alternatively, the dispersing step may be accomplished by lyophilizing the mixture. Lyophilization is dehydration of frozen material under vacuum.

Prior to the dispersing step, the matrix may be pre-equilibrated with the solvent in which the osteogenic protein has been dispersed. The method may further include the steps of forming the product of the dispersion step into a shape with predetermined dimensions; and implanting the formed product into a mammal. Implantation of the device results in the induction of endochondral bone having essentially the shape of the formed product.

Lastly, the invention is embodied as a method of inducing endochondral bone growth in a mammal comprising the step of implanting in the mammal, either surgically or otherwise, at a location where bone formation is desired, porous matrix material containing dispersed osteogenic protein of a nature described herein.

BRIEF DESCRIPTION OF THE DRAWINGS

The foregoing and other objects of the invention, the various features thereof, as well as the invention itself, may be more fully understood from the following description when read together with the accompanying drawings in which.

DETAILED DESCRIPTION

Figure 1:
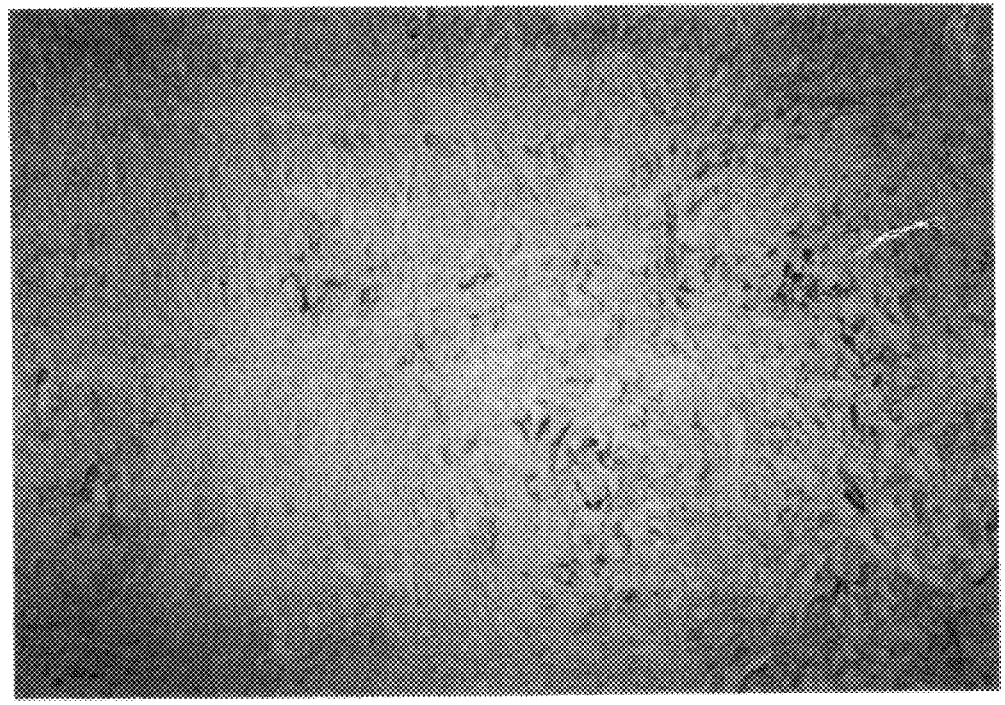
FIG. 1 is a photomicrograph of a collagen-GAG implant without osteogenic protein showing the infiltration of only mesenchymal cells.

This invention provides an osteogenic device capable of inducing de novo osteogenesis when implanted in the mammalian body. The device enabled and disclosed herein will permit the physician to obtain optimal predictable bone formation to correct, for example, acquired and congenital craniofacial and other skeletal or dental anomalies (Glowacki et al. (1981) Lancet 1:959–963). The device may be used to induce local endochondral bone formation in non-union fractures and in other clinical applications including periodontal applications where bone formation is required. Other potential clinical applications include contour augmentation, spinal fusion, and orthopedic reconstructive surgury.

The osteogenic device useful for inducing de novo bone growth comprises osteogenic protein dispersed within a cross-linked matrix of collagen and GAG polymers. Osteogenic protein may be obtained using the methods disclosed in U.S. patent application Ser. No. 179,406, filed Apr. 8, 1988 (entitled "Osteogenic Protein"); PCT application No. US89/01469 (entitled Biosynthetic Osteogenic Proteins and Osteogenic Devices Containing Them), and PCT Application No. US89/01453, (entitled "Osteogenic Devices"). Both PCT applications were filed Apr. 7, 1989. Alternatively, extracts rich in osteogenic protein useful in fabricating devices may be obtained as disclosed in U.S. Pat. No. 4,294,753 to Urist. The disclosure of these documents is incorporated herein by reference. Alternatively, any other proteins with osteogenic activity in mammals may be used. Further, skilled genetic engineers can isolate genes from cDNA or genomic libraries which encode appropriate amino acid sequences, or construct DNAs from oligonucleotides, and then can express them in various types of host cells, including both procaryotes and eucaryotes, to produce large quantities of active proteins capable of inducing bone formation in mammals including humans.

The matrix material is composed of collagen polymers and glycosaminoglycans. It may be prepared essentially as described by Yannas et al. in U.S. Pat. Nos. 4,280,954 and 4,448,718, the teachings of which are herein incorporated by reference. Alternatively, the GAG-collagen porous matrix material may be commercially obtained. For example, porous microcarriers of collagen-GAG cross-linked copolymer intended for in vitro use (Informatrix™) are available from the Biomat Corporation (Belmont, Mass.). This material was developed originally for medical wound dressing applications, and includes collagen extracted from bovine hide, and 8% (w/w) chondroitin 6-sulfate. Other GAG species, such as heparin or hyaluronic acid, can be incorporated on a custom basis.

Briefly, collagen is a major protein constituent of connective tissue and has been widely used in various medical and surgical applications such as for surgical protheses and graft fabrication. This protein is easily resorbed due to its susceptibility to proteolytic digestion by collagenases present at the implantation site. It may be in the form of macroscopic fibers which can be chemically and mechanically separated from non-collagenous tissue components. Collagen derived from any source is suitable for use with this invention, including insoluble collagen, acid-soluble collagen, collagen soluble in neutral or basic aqueous solutions, as well as those collagens which are commercially available. Typical animal sources include calfskin, bovine achilles tendon, cattle bones, and rat tail tendon.

Glycosaminoglycans (GAGs) or mucopolysaccharides are hexosamine-containing polysaccharides of animal origin. Chemically, GAGs are made up of residues of hexosamines glycosidically bound and alternating in a more-or-less regular manner with either hexuronic acid or hexose moieties (see, e.g., Dodgson et al. in *Carbohydrate Metabolism and its Disorders* (Dickens et al., eds.) Vol. 1, Academic Press (1968)). Useful GAGs include hyaluronic acid, heparin, heparan sulfate, chondroitin 6-sulfate, chondroitin 4-sulfate, dermatan sulfate, and keratan sulfate. Other GAGs are suitable for forming the matrix described herein, and thoses skilled in the art will either know or be able to ascertain other suitable GAGs using no more than routine experimentation. For a more detailed description of mucopolysaccharides, see Aspinall, *Polysaccharides*, Pergamon Press, Oxford (1970).

Collagen can be reacted with a GAG in aqueous acidic solutions. These reactions can be carried out at room temperature. Typically, small amounts of collagen, such as 0.3% by weight, are dispersed in a dilute acetic acid solution and thoroughly agitated. The GAG is then slowly added, for example dropwise, into the aqueous collagen dispersion, which causes the coprecipitation of collagen and GAG. The coprecipitate is a tangled mass of collagen fibrils coated with GAG. This tangled mass of fibers can be homogenized to form a homogeneous dispersion of fine fibers and then filtered and dried. The conditions for maximum attachment of GAGs to collagen without significant partial denaturation (gelatinization) were found to be a pH of about 3 and a temperature of about 37° C. Although these conditions are preferred, other reaction conditions which result in a significant reaction between collagen and a mucopolysaccharide are also suitable.

While the coprecipitation method described above is preferred, collagen and GAGs can be reacted in other ways. The essential requirement is that the two materials be intimately contacted under conditions which allow the GAGs to attach to the collagen chains. Another suitable technique is to coat collagen with GAGs, such as by dipping articles formed from collagen into a solution of GAG. A suitable variation of the latter technique involves prior coating with collagen of an article, sheet, film or tube fabricated from a non-collagenous material, such as a synthetic, natural or modified natural polymer, followed by dipping of the collagen-coated article, sheet, film or tube into the GAG solution. Still another suitable method is to intimately mix collagen with GAG, with each component in the form of a dry powder.

It will be clear that the collagen-GAG product prepared as described above can be formed into sheets, films, tubes and other shapes or particles for its ultimate application.

To gain any significant increase in resistance to collagen resorption, it is necessary to have at least about 0.5% by weight of GAG bound to the collagen chains. The upper limit may be set by the sites on collagen which are available for GAG attachment. For composites wherein the GAG is chondroitin 6-sulfate, levels of about 28% by weight have been achieved; with hyaluronic acid, on the other hand, the upper limit achieved is about 25%.

Reaction with the GAGs also provides collagen with another valuable property, i.e., inability to provoke an immune reaction (foreign body reaction) from an animal host. To convert collagen into a material which, when implanted, would not be recognized as a foreign body requires reacting it with at least about 1% by weight of GAG.

Insolubility of the collagen-GAG products can be raised to the desired degree by covalently cross-linking these materials. In general, any covalent cross-linking method suitable for cross-linking collagen is also suitable for cross-linking these composite materials. Such covalent cross-linking serves to prevent dissolution of mucopolysaccharide in aqueous solutions thereby making the materials useful for surgical prostheses, etc.

Covalent cross-linking also serves to raise the resistance to resorption of these materials. The exact function of cross-linking is not understood in this regard, but it may be that cross-linking anchors the GAG units to sites on the collagen chain which would normally be attacked by collagenase. Another possible explanation is that cross-linking tightens up the network of collagen fibers and physically restricts the diffusion of enzymes capable of degrading collagen.

It has been found that the cross-linked composites should have an $M_C$ of between about 800 and about 60,000. Materials with $M_C$ values below about 800 or above about 60,000 suffer significant losses in their mechanical properties. Composites with an $M_C$ of between about 5,000 and about 10,000 appear to have a good balance of mechanical properties, and so this is the preferred range of cross-linking for products requiring such a balance of properties.

Covalent cross-linking can be achieved by many specific techniques with the general categories being chemical, radiation and dehydrothermal methods. An advantage to most cross-linking techniques contemplated, including glutaraldehyde cross-linking and dehydrothermal cross-linking, is that they also serve in preventing bacterial growth on the materials. Thus, the composites are being sterilized at the same time that they are cross-linked.

One suitable chemical method for covalently cross-linking the collagen-GAG composites is known as aldehyde cross-linking. In this process, the materials are contacted with aqueous solutions of aldehyde, which serve to cross-link the materials. Suitable aldehydes include formaldehyde, glutaraldehyde and glyoxal. The preferred aldehyde is glutaraldehyde because it yields the desired level of cross-link density more rapidly than other aldehydes and also is capable of increasing the cross-link density to a relatively high level. Immersing the composites in aldehyde solutions causes partial removal of the polysaccharide component by dissolution thereby lessening the amount of polysaccharide in the final product. Unreacted aldehydes should be removed from the collagen-GAG materials since residual aldehydes are quite toxic.

Other chemical techniques which are suitable include carbodiimide coupling, azide coupling, and diisocyanate cross-linking.

A preferred cross-linking method is referred to herein as a dehydrothermal process. In dehydrothermal cross-linking, it is not necessary to add external cross-linking agents. The key is to dehydrate the product to be cross-linked to a moisture content of less than about 1%. The amount of water which must be removed will vary with many factors, but, in general, sufficient water to achieve the desired density of cross-linking must be removed. Thus, the collagen-GAG product can be subjected to elevated temperatures and/or vacuum conditions until the moisture content is reduced to extremely low levels. In the absence of vacuum, temperatures above about 80° C., and preferably above 90° C., can be used. At 23° C., a vacuum of at least about $10^{-5}$ mm Hg, and preferably below $10^{-6}$ Hg, is suitable. Elevated temperature and vacuum can be also used in combination; this, in fact, is the most expeditious route and is therefore preferred. With a vacuum of at least about $10^{-5}$ mm Hg, it is preferred to use a temperature of at least about 35° C. In general, the materials are subjected to the elevated temperatures and vacuum conditions until the degree of insolubility desired is obtained. The higher the temperature, the lower is the vacuum required to arrive at a given cross-link density, and vice versa. A typical cross-linking process to attain an $M_C$ between about 5,000 and 10,000 involves subjecting the collagen-GAG material to a temperature of 95° C. and a vacuum of 0.01 mm Hg for 24 hours. This dehydrothermal cross-linking process overcomes certain disadvantages of the aldehyde cross-linking method and produces composites having relatively large amounts of GAG strongly bound to the collagen chain.

Optimum mechanical properties are obtained for pure collagen materials with $M_C$, the average molecular weight between cross-links, between 5,000 and 10,000. Certain collagen-GAG composites prepared by the dehydrothermal cross-linking process have superior elongation at break, strength, and toughness compared to collagen with similar values of $M_C$.

Based upon resistance to resorption, freedom from foreign body reaction, mechanical properties and blood-compatibility, cross-linked composites should contain at least about 0.5% bound GAG. Those composites containing between about 6% and about 15% of a sulfate-containing GAG are particularly preferred because of their outstanding properties, including blood-compatibility. The percentage of GAG specified herein is that obtained when the measurement is made immediately after cross-linking. With thorough washing, any GAG which is not covalently bound can be removed.

When dry, the commercially available porous microcarriers contain about 5 g of collagen per liter of bead internal volume. They exhibit about 20% shrinkage by volume after hydration and suspension in phosphate buffered saline (PBS). One gram of hydrated microcarriers in PBS occupies a settled bed volume of about 250 ml. The material is roughly 99.5% void volume. This makes it very efficient in terms of the potential cell mass that can be grown per gram of microcarrier.

Particles are essentially spherical, with diameters of about 500 µm. Scanning electron microscopy shows pores of about 20 µm on the surface and 40 µm on the interior. The interior is made up of both fibrous and sheet-like structures, providing surfaces for cell attachment. The voids interconnect, providing access to the cells throughout the interior of the particle.

When suspended in PBS or culture medium, the microcarriers are nearly neutrally buoyant. Small amounts of entrapped air or changes in solution temperature are sufficient to bias the particles toward floating or sinking. The spherical collagen-GAG material is precipitated in 70% ethanol to replace air in the beads with a liquid. The ethanol is then displaced with buffered saline or 30%–55% acetonitrile acidified with trifluoroacetic acid (TFA) or other acids. Acetonitrile (ACN) is an organic solvent, capable of denaturing proteins without affecting their primary structure. It is a common reagent in high performance liquid chromatography, and is used to elute proteins from silica based column by perturbing hydrophobic interactions.

If the matrix material is to include osteogenic protein, the protein is added in either Tris buffered saline (TBS) or acetonitrile/TFA is then added to the collagen-GAG material preequilibrated in the same buffer. The mixture is incubated at 4° C. and then lyophilized. This matrix material may be made heavier by adding bovine insoluble collagen. The resulting matrix material is a fine powder, insoluble in water, and comprising nonadherent particles.

The matrix material preferably has the characteristics set forth below in TABLE 1.

TABLE 1

| Scanning Election Microscopy | |
|---|---|
| pore size | 1–100 µ |
| particle size | 74–420 µ |
| pits | <$10^3$ nm |
| Mercury Infusion Data | |
| pore size | 2.390 ml/g |
| bulk density | 0.214 g/ml |
| skeletal density | 0.830 g/ml |
| surface area | 0.3226 g/ml |
| pore area | 0.214 m²/g |
| pore diameter | 41.988 µg |

Practice of the invention requires the implantation of the matrix, e.g., surgically, to serve as a template for bone formation in various orthopedic, periodontal, and reconstructive procedures, or as a collagenous coating for implants. The matrix may be shaped as desired in anticipation of surgery or shaped by the physician or technician during surgery. The material may also be injected into a site where bone growth is desired.

Alternatively, the material may be coated or adsorbed on a prosthetic implant to promote implant/bone adhesion. Useful implants are constructed of inert materials such as ceramic, metals such as titanium, cadmium, nickel, or cobalt, or polymers such as polyglycolic acid or polylactic acid. Upon the addition of a heat-activated glue such as methyl cellulose, the material becomes solidified after implantation or when placed at 37° C.

Thus, the material may be used for subcutaneous, intraperitoneal, or intramuscular implants; it may be shaped to span a non-union fracture or to fill a bone defect. The material encourages cell motility, cellular biosynthetic functions, and cell division. Hence, osteoblasts may be induced to migrate from viable bone to the material. In addition, the cross-linked GAG material has a negative surface charge which enhances cell attachment. Furthermore, osteoblasts synthesize fibronectin, a cellular adherence protein that binds collagen, thereby enhancing the ability of the migrating osteoblasts to adhere to the implant.

In bone formation procedures, the matrix material is slowly absorbed by the body and is replaced by bone in the shape of or very nearly the shape of the implant. The matrix material also may be used to induce bone induction, and as a sustained release carrier.

The osteogenic device may comprise a shape-retaining solid made of loosely adhered particulate material. It may also comprise a molded, porous solid, or simply an aggregation of close-packed particles held in place by surrounding tissue. Insoluble collagen or inert polymers added to the collagen-GAG-osteogenic protein particles may increase the density of the device. In addition, a glue or solidifying agent including methyl cellulose, (e.g., Methocel, Dow Chemical co.), may be added. It is preferable to shape the matrix into the desired form of the new bone or to have dimensions which span non-union defects.

Figure 2:
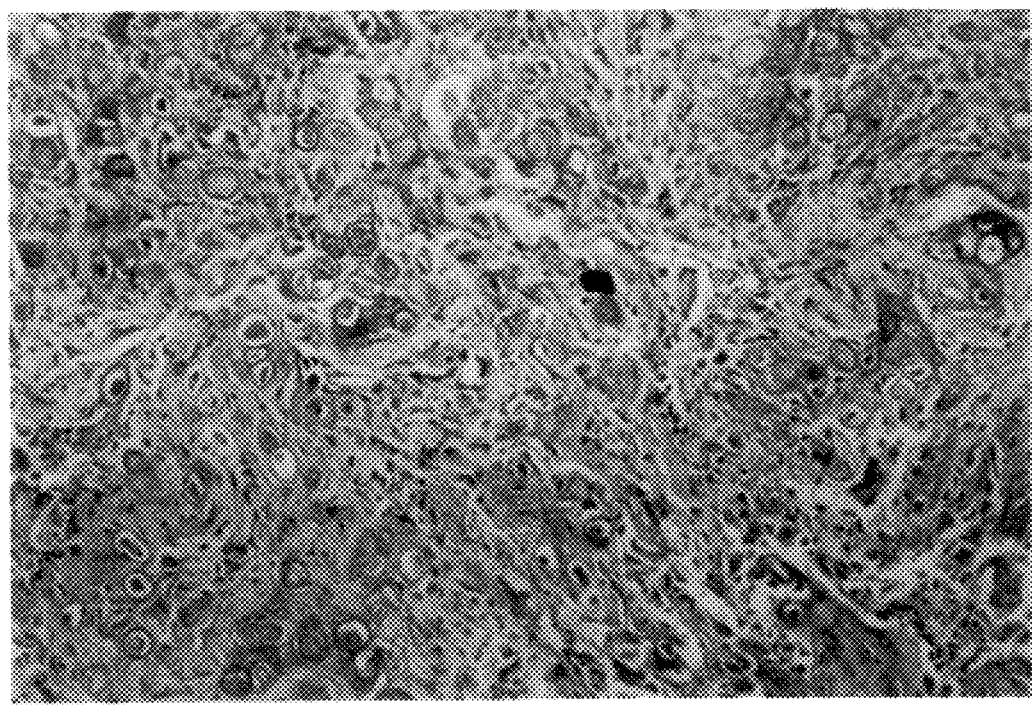
FIG. 2 is a photomicrograph of a collagen-GAG matrix including osteogenic protein showing the presence of osteoblasts (arrows), bone formation, and vascular invasion.

The functioning of the various matrices prepared by any one of the above methods can be evaluated with an in vivo rat bioassay as described in the patent applications referenced above. Briefly, the lyophilized matrix implant is placed into a subcutaneous wound which is then closed with metallic clips. Implants are removed from the rat on day 12 after implantation and evaluated histologically for evidence of bone formation. FIG. 1 demonstrates that only mesenchymal cells will be associated with a collagen-GAG implant that does not include osteogenic protein, while FIG. 2 shows the ultimate development of endochondral bone in an implant which included osteogenic protein. Twelve day implants are usually sufficient to determine whether the implants contain newly induced bone.

Alkaline phosphatase activity may be used as a marker for osteogenesis (Reddi et al. (1972) Proc. Natl. Acad. Sci. (U.S.A.) 69:1601–1605). The enzyme activity may be determined spectrophotometrically after homogenization of the implant. The activity peaks at 9–10 days in vivo and thereafter slowly declines. Implants showing no bone development by histology have little or no alkaline phosphatase activity under these assay conditions. The assay is useful for quantitation and obtaining an estimate of bone formation quickly after the implants are removed from the rat.

Alternatively, the amount of bone formation can be determined by measuring the calcium content of the implant.

Such studies have established that the collagen-GAG particles are still present after 12 days in vivo. As shown in FIG. 1 and in TABLE 2, control matrices without osteogenic protein did not induce bone growth in vivo; however, some mesenchymal cells recruited by the matrix were present. In comparison, collagen-GAG matrices, when formulated with osteogenic protein preparations in either TBS or acetonitrile/ TFA, induced bone differentiation upon implantation as shown in FIG. 2 and in TABLE 2.

TABLE 2

| Formula. Methods | (+) Growth/# Samples | % Bone Growth |
| --- | --- | --- |
| Acetonitrile/TFA | | |
| (+) OP | 3/5 | 60 |
| | | 50 |
| | | 10 |
| (−) OP | 0/5 | 0 |
| Tris-Buffer Saline | | |
| (+) OP | 3/3 | 80 |
| | | 70 |
| | | 10 |
| (−) OP | 0/3 | 0 |

Successful implants exhibit a controlled progression through the stages of matrix induced endochondral bone development including: (1) transient infiltration by polymorphonuclear leukocytes on day one; (2) mesenchymal cell migration and proliferation on days two and three; (3) chondrocyte appearance on days five and six; (4) cartilage matrix formation on day seven; (5) cartiliage calcification on day eight; (6) vascular invasion, appearance of osteoblasts, and formation of new bone on days nine and ten (see FIG. 2). If left beyond day 12 there is the appearance of osteoblastic and bone remodeling and dissolution of the implanted matrix on days twelve to eighteen; and hematopoietic bone marrow differentiation in the ossicle on day twenty-one. The results show that the shape of the new bone substantially conforms to the shape of the implanted matrix.

The collagen-GAG material is resorbed, making space for newly formed bone to occupy. The size of the bone formed is the size of the implant prepared. An implant is considered positive when the material is localized at one site. Variation in response is explained by difficulties in the implant procedure because of the low density of the prototype matrix material and difficulty in maintaining it at a subcutaneous site.

Details of how to make and how to use the materials of the invention are disclosed below.

EXAMPLES

A. Preparation of CollaQen-GAG Matrix

The cross-linked collagen-GAG material is prepared by previously published procedures of Yannas. (U.S. Pat. No. 4,350,629). Briefly this entails the following procedures.
1. Preparation of the Collagen Bovine collagen is prepared by the methods of Komanowsky et al. (J. Amer. Leather Chemists Assn. (1974) 69:410–422). 0.55 g of freeze-dried collagen is ground in a Wiley mill (A. H. Thomas Co., Phila. PA) to a 60 mesh particle size. It is added to 200 ml of 0.05 M aqueous acetic acid. This solution is stirred for 60 minutes in an ice-jacketed blender (Eberbach Corp., Ann Arbor, Mich.) on a 2-speed power unit (Waring Co., Hartford, Conn.) set on high speed with the line voltage reduced to 60 volts. Following this blending step, the solution is placed in a tightly closed glass jar and the collagen is allowed to swell for 72 hours at 4° C.
2. Preparation of Collagen-Chondroitin 6-Sulfate Coprecipitates Collagen 0.3% (wt/vol) dispersed in 0.05 M acetic acid is thoroughly agitated with a Teflon stirrer at 23° C. While the dispersion was mixing, 1% chondroitin 6-sulfate (wt/vol) in 0.05 M acetic acid pH 3.2 is added dropwise from a buret at the rate of about 0.1 ml per second. The addition of chondroitin 6-sulfate causes collagen to coprecipitate forming a tangled mass of collagen fibrils coated with GAG. When 90% by weight of collagen is coprecipitated in this manner with 10% by weight chondroitin 6-sulfate, a systematic mass balance shows that about 95% of the added chondroitin 6-sulfate is coprecipitated.

After coprecipitation, the tangled mass of fibrils is homogenized in a Waring Blender until the fibrils are about 1 mm in length. The mixture of fibrils in 0.05 M acetic acid separates into two phases when left unagitated for more than five minutes, so that mixing is required before filtration. Filtration is performed by filtering the collagen-mucopolysaccharide dispersion under vacuum through a Buchner funnel containing Schleicher and Schuell (Keene, New Hampshire) filter paper No. 576. The coprecipitate is allowed to dehydrate under atmospheric conditions until the moisture content was about 20% by weight.

If it is desirable to maintain high porosity in the product, the composites can be freeze dried. Typical conditions are a temperature of −50° C. and a vacuum of 0.06 mm Hg.

3. Aldehyde Cross-linking

Method A

Coprecipitated collagen-chondroitin 6-sulfate as prepared in EXAMPLE 2 is covalently cross-linked by immersing it in a 0.02 M solution of glutaraldehyde. This treatment effectively immobilizes a fraction of the polysaccharide component on the collagen fibrils or molecules. Cross-linking is evidenced by the inability to remove the polysaccharide from the aldehyde-treated film by prolonged washing with a phosphate buffer solution containing 0.4 M sodium chloride, pH 7.4, which is a well known solvent of chondroitin 6-sulfate. Unreacted aldehydes are removed by treatment with a solution of 5,5 dimethyl-1,3-cyclohexane dione (dimedone). Evaporation of the water leaves behind a film containing up to about 10% by weight polysaccharide.

Method B

A solution of 25% glutaraldehyde ("Baker-analyzed" reagent grade, J. T. Baker Co., Philadelphia, Pa.) in distilled water is prepared. A sufficient quantity of thins solution is added to the acidic collagen solution to comprise 0.5% (vol/vol) glutaraldehyde. The glutaraldehyde solution is added while the dispersion was blended for one hour in an overhead blender (Hamilton Beach Div. of Scovill, Washington, N.C.) set on the low speed with the line voltage reduced to 60 volts.

0.0578 g chondroitin 6-sulfate is dissolved in 10 ml of 0.05 M acetic acid. This solution is added to 175 ml of the glutaraldehyde-treated collagen dispersion. The addition is performed over a period of 5 minutes while the dispersion is being blended in the overhead blender.

Shortly thereafter, the dispersion is filtered in a Buechner funnel. This filtering step is completed in about 20 minutes. The resulting wet membrane is then air-dried and milled to a 60 mesh particle size. It is dispersed in physiological saline solution (0.15 M NaCl, pH 7).

4. Dehydrothermal Cross-linking

The product of EXAMPLE 3 is placed in a vacuum oven and exposed to a temperature of 115° C. and a vacuum of at least 0.3 mm Hg for 48 hours. At the end of this treatment, less than 10 weight percent of the polysaccharide originally incorporated into the film can be removed by 48-hour immersion in distilled water, a solvent for chondroitin 6-sulfate.

B. Preparation of Osteogenic Material

The osteogenic protein may be obtained using the methods disclosed in U.S. patent application Ser. No. 179,406 filed Apr. 8, 1988; PCT application No. US89/01469 (entitled "Biosynthetic Osteogenic Proteins and Osteogenic Devices Containing Them"), and PCT Application No. US89/01453, (entitled Osteogenic Devices). Both PCT applications were filed Apr. 7, 1989. Alternatively, extracts rich in osteogenic protein useful in fabricating devices may be obtained as disclosed in U.S. Pat. No. 4,294,753 to Urist.

C. Formulation of Osteogenic Protein within the Collagen-GAG Material

The collagen-GAG material assuming the form of small beads is expanded in 70% ethanol to replace air in the beads with a liquid. The beads are prepared as follows: about 100 ml of 70% ethanol (vol/vol) in sterile water is added to a 50 ml bottle of collagen-GAG beads (Biomat Corporation, Belmont, Mass.). The beads are allowed to settle at 4° C. The top layer of ethanol is decanted and replaced with fresh 70%. This step is repeated until all of the particles have sunk. Alternatively, the particles may be prepared by centrifugation at low speed (e.g. ×500 g).

The 70% ethanol is then displaced from the beads by 50 mm Tris-HCl, 0.15 M NaCl, pH 7.0 (TBS), or by 30% to 50% acetonitrile containing 0.1% trifluoroacetic acid (TFA). The displacement of ethanol with buffer is accomplished by repeated slow-speed centrifugation, decanting, and exchanging buffers. This is done at 4° C. to aid in the preparation process and to avoid possible degradation of the collagen-GAG material.

Osteogenic protein is then adhered to the matrix material. The osteogenic protein preparations adhered to the matrix material are (1) the sephacryl active fraction (this fraction induces bone growth in rat at 5 to 20 µg/implant); and (2) the heparin-sepharose fraction (this fraction induces bone in rat at 1 to 10 µg/implant). The osteogenic protein may be formulated onto the collagen-GAG matrix by.one of the following methods:

1. Acetonitrile/TFA Lyophilization

To 0.2–0.3 ml of matrix preequilibrated with acetonitrile/TFA buffer is added 200 pl of osteogenic protein fractions in 50% acetonitrile containing 0.1% TFA. The mixture is incubated at 4° C. for 16 hours. It is then lyophilized.

2. TBS Binding/Lyophilization

To 0.2–0.3 ml of matrix equilibrated with TBS buffer is added 200 pl of TBS buffer. 10 µl of 50% acetonitrile containing 0.1% TFA, which contains osteogenic protein preparation in a concentrated amount is added. The pH should then be adjusted to 7.0. This mixture is incubated at 24° C. for 2 hours and then 4° C. for 16 hours before lyophilization.

D. Bioassay for Bone Induction

The bioassay for bone induction as described by Sampath and Reddi (Proc. Natl. Acad. Sci. USA (1983) 80: 6591–6595), herein incorporated by reference, may be used to monitor endochondral bone differentiation activity. This assay consists of implanting the bovine test samples xenogenically in subcutaneous sites in recipient rats under ether anesthesia. Male Long-Evans rats, aged 28–32 days, were used. A vertical incision (1 cm) is made under sterile conditions in the skin over the thoracic region, and a pocket is prepared by blunt dissection. Approximately 25 mg of the test sample is implanted deep into the pocket and the incision is closed with a metallic skin clip. The heterotropic site allows for the study of bone induction without the possible ambiguities resulting from the use of orthotopic sites. The day of implantation is designated as day one of the experiment.

Implants are removed from the rat on day 12 after implantation and evaluated histologically for evidence of bone formation.

E. Histology

Resected implants are fixed in Bouins Solution, embedded in paraffin, cut into 6–8 mm sections, and stained with toluidine blue or hemotoxylin/eosin.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An osteogenic device for inducing local bone or cartilage formation in a mammal, said device comprising:
   (a) biocompatible, synthetic, porous matrix, said matrix comprising a polymer of collagen and glycosaminoglycan crosslinked ex vivo to an $M_C$ value of about 800 to about 60,000 and comprising greater than 1% by weight of said glycosaminoglycan;
   (b) osteogenic protein capable of inducing endochondral bone formation in a mammal dispersed within said matrix; and
   (c) solidifying agent.

2. The device of claim 1, wherein said solidifying agent solidifies at a temperature greater than ambient temperature.

3. The device of claim 1, wherein said solidifying agent is methyl cellulose.

4. The device of claim 1, wherein said osteogenic protein is OP-1.

5. The device of claim 1, wherein said glycosaminoglycan comprises at least 5% by weight of said polymer.

6. The device of claim 5, wherein said glycosaminoglycan comprises from about 6% to about 15% by weight of said polymer.

7. The device of claim 1, wherein said glycosaminoglycan is selected from the group consisting of chondroitin 4-sulfate, chondroitin 6-sulfate, hyaluronic acid, dermatan sulfate, keratan sulfate, heparin, heparan sulfate, and combinations thereof.

8. The device of claim 1, wherein said glycosaminoglycan comprises a sulfate group.

9. The device of claim 1, wherein said glycosaminoglycan comprises chondroitin 6-sulfate.

10. The device of claim 1, wherein said polymer is cross-linked to an $M_C$ value of between 5,000 and 10,000.

11. The device of claim 1, wherein said osteogenic protein comprises a pair of polypeptide chains disulfide bonded to form a dimeric species and further wherein each of said polypeptide chains is characterized as having at least seven cysteine residues in the same relative positions as the seven cysteine skeleton sequence:

```
    1        10        20        30        40
    CXXXXLXVXFXDXGWXXWXXXPXGXXAXYCXGXCXXPXXX
              50        60        70        80
    XXXXXNHAXXQXXVXXXNXXXXPXXCCXPXXXXXXXXLXX
              90       100
    XXXXXVXLXXYXXMXVXXCX
``` wherein each said X is an amino acid, such that said osteogenic protein induces local bone or cartilage formation in a mammal when disposed within said matrix implanted in said mammal.

12. The device of claim 1, wherein said osteogenic protein comprises a pair of polypeptide chains disulfide bonded to form a dimeric species and further wherein each of said polypeptide chains is characterized as having at least six cysteine residues in the same relative positions as the six cysteine skeleton sequence:

```
    1        10        20        30        40
         LXVXFXDXGWXXWXXXPXGXXAXYCXGXCXXPXXX
              50        60        70
         XXXXXNHAXXQXXVXXXNXXXXPXXCCXPXXXXXX
              80        90       100
         XXLXXXXXXXVXLXXYXXMXVXXCXCX,
``` wherein each said X is an amino acid, such that said osteogenic protein induces local bone or cartilage formation in a mammal when disposed within said matrix implanted in said mammal.

13. The device of claim 1, wherein said osteogenic protein comprises a pair of subunits constituting a dimer under oxidizing conditions, one of said subunits having an amino acid sequence comprising the amino acid sequence, or conservative amino acid substituted variants thereof,

```
    1        10        20        30        40        50
    STGSKQRSQNRSKTPKNQEALRMANVAENSSSDQRQACKKHELYVSFRDL
              60        70        80        90       100
    GWQDWIIAPEGYARYYCEGECAFPLNSYMNATNHAIVQTLVHFINPETVP
             110       120       130
    KPCCAPTQLNAISVLYFDDSSNVILKKYRNMVVRACGCH
``` such that said subunit, when in combination with the second of said subunits, induces local bone or cartilage formation in a mammal when disposed within said matrix implanted in said mammal.

14. The device of claim 1, wherein said polymer is selected from the group consisting of Type I collagen, Type II collagen, and mixtures thereof.

15. The device of claim 1, wherein said osteogenic protein comprises a pair of subunits constituting a dimer under oxidizing conditions, one of said subunits having an amino acid sequence sufficiently duplicative of the amino acid sequence of OP1:

```
    1        10        20        30        40
       STGSKQRSQNRSKTPKNQEALRMANVAENSSSDQRQACKK
              50        60        70        80
       HELYVSFRDLGWQDWIIAPEGYARYYCEGECAFPLNSYMN
              90       100       110       120
       ATNHAIVQTLVHFINPETVPKPCCAPTQLNAISVLYFDDSS
             130
       NVILKKYRNMVVRACGCH
``` such that said subunit, when in combination with the second of said subunits, induces local bone or cartilage formation in a mammal when disposed within said matrix implanted in said mammal.

* * * * *